United States Patent [19]

Bowman et al.

[11] Patent Number: 5,792,068
[45] Date of Patent: Aug. 11, 1998

[54] MEDICAL MONITOR WITH FAILURE PROTECTION

[75] Inventors: Bruce R. Bowman, Eden Prairie; Peter Stasz, St. Paul, both of Minn.

[73] Assignee: EdenTec, Inc., Eden Prairie, Minn.

[21] Appl. No.: 157,737

[22] Filed: Nov. 24, 1993

Related U.S. Application Data

[63] Continuation of Ser. No. 902,899, Jun. 23, 1992, abandoned.

[51] Int. Cl.⁶ .................................................. A61B 5/04
[52] U.S. Cl. .................................. 600/536; 600/529
[58] Field of Search ............................ 128/716–723, 128/901; 607/42; 606/32–34

[56] References Cited

U.S. PATENT DOCUMENTS

| | | | |
|---|---|---|---|
| 4,091,818 | 5/1978 | Brownlee et al. | 607/9 |
| 4,228,803 | 10/1980 | Rickards | 607/25 |
| 4,235,242 | 11/1980 | Howson et al. | 128/901 |
| 4,506,678 | 3/1985 | Russell et al. | 128/723 |
| 4,803,997 | 2/1989 | Bowman | 128/723 |
| 4,934,377 | 6/1990 | Bova et al. | 128/696 |

Primary Examiner—Michael Peffley
Attorney, Agent, or Firm—Nawrocki, Rooney & Sivertson, P.A.

[57] ABSTRACT

An apparatus for and method of monitoring respiration of a patient using impedance changes of the body to indicate respiration events. The impedance changes are measured by applying a carrier signal across the thorax of the patient. The carrier is periodically interrupted to produce a quiet period. A first level detector assumes the presence of EMI if the signal present during the quiet period exceeds a predetermined threshold. A second level detector senses the presence of substantial high frequency EMI. At initial power up, a third level detector checks for presence of signal before the carrier drive is applied. A fourth test circuit checks for the hang up of the differential amplification circuit.

7 Claims, 12 Drawing Sheets

MEDICAL MONITOR WITH FAILURE PROTECTION

RELATED APPLICATIONS

This is a continuation of U.S. application Ser. No. 07/902,899, filed Jun. 23, 1992, and entitled MEDICAL MONITOR WITH FAILURE PROTECTION, now abandoned.

BACKGROUND OF THE INVENTION

1. Field of the Invention

The present invention generally relates to medical devices and more particularly relates to medical devices used to monitor patient respiration.

2. Description of the Prior Art

It has been known for some time that it is desirable to monitor patients to provide an alarm to attending personnel upon cessation of or the presence of grossly irregular respiration. Often monitoring devices are employed during the sleep of patients who are prone to central sleep apnea. Many of these patients are children or infants. An alarm condition indicates that remedial action is quickly needed to restore normal respiration before the patient suffers irreversible damage or death as a result of oxygen deficiency.

The early monitoring devices employed a number of sensor types to determine abnormal respiration. Sensors to measure airflow, blood gas composition, and stretching of the thorax have all been used with some degree of success. However, the most widely employed monitoring technique in current clinical use measures changes of impedance across the thorax of a patient. This is accomplished by passing a small current through the thorax between two surface electrodes. As a patient inhales, the lungs fill with air, the thorax becomes less conductive, and the measured resistance across the thorax increases. Upon exhaling, the reverse happens, and the resistance decreases.

In the most practical systems, this small current is an alternating current having a frequency of 25–100 KHz. By using this frequency range, the electrical circuitry can quite readily reject a number of noise components located on either side of the basic carrier frequency.

U.S. Pat. No. 4,803,997, issued to Bowman and incorporated herein by reference, addresses the presence of an artifactual respiratory signal, which recurs at the basic heart rate of the patient, often referred to as cardiac artifact. In Bowman the cardiac artifact signal is explicitly sensed and processed using separate detection circuitry to ensure that the cardiac artifact is not treated as a respiration signal.

Rejection of the cardiac artifact using the Bowman invention provides a significant improvement. However, even with extensive filtering and shielding techniques, it is known that problems still exist with other sensing failures caused by electromagnetic interference (i.e. EMI) that is strong enough to interfere with the normal behavior of the monitoring system. Because of the metallic equipment cabinet which houses the respiration signal processing circuitry, most often the problem arises from the field of the EMI tending to induce a current in the conductors which electrically couple the monitoring electrodes on the patient with the monitoring hardware. This tendency could be reduced by lowering the overall impedance of the system, but this is most determined by the relatively fixed impedance across the thorax of the patient. Other means for entry of the interference include the power cord, improper grounding, and possible breaks in the shielding provided by the equipment cabinet.

The greatest danger of EMI induced false signals is that they may be erroneously sensed as normal respiration signals from the patient. As a result, the patient could be experiencing difficulty with respiration or even an apnea event without detection by the monitoring system.

The first means of defense against the inaccuracies associated with EMI is prevention. This involves cautioning the operator or attendant of the monitoring system to avoid potential EMI sources. Whereas this is an excellent approach and necessary in any event, it does not provide any positive, ongoing feedback to the operator that all EMI sources have been avoided. The operator may indeed have diligently attempted to avoid EMI without success and have no way to be warned of the failure of his attempt. Even more likely is that the operator has properly located and installed the system thereby avoiding EMI only to have EMI appear later as the result of a subsequent event, such as the turning on of an appliance or piece of electronic equipment.

Typical sources of unpredictable, high levels of EMI energy include police radio, dispatching (e.g. cabs or delivery services), amateur radio operations, and citizen band radio. Other sources are AM and FM radio transmission towers and microwave communication links.

SUMMARY OF THE INVENTION

The present invention overcomes the disadvantages found in the prior art by providing a device for monitoring the respiration of a patient, which provides protection against the likelihood that a component failure or EMI generated false signals will be mistakenly assumed to be respiration signals from the patient being monitored.

In the preferred mode, the present invention employs a regulated oscillator to supply a square wave signal, which is applied across the thorax of the patient to be monitored by surface electrodes. Monitoring circuitry senses changes in impedance of the thorax by measuring changes in voltage of the square wave signal. The system employs four (4) features which tend to ensure accuracy and reliability of the apnea monitoring operation.

A first feature functions as a portion of the initial power on sequence. Application of the 31 KHz carrier to the patient cable is delayed for a period of time, preferably about ten (10) seconds. During this period of delay, the output of the respiration monitor circuitry is sampled to determine whether a signal is present. If not, the system has passed the initial test. However, if an output signal is present during this time, it signifies a hardware failure or alternatively presence of a strong EMI signal on the patient cable. A special hardware alarm is provided to alert the operator.

A second feature amplifies and high pass filters the input from the patient cable. In this manner, presence of strong high frequency EMI may be detected and an alarm provided to the operator. This circuitry functions constantly during use of the apnea monitor. Even though the EMI which it detects is substantially beyond the frequencies of interest, strong signals in this region, and sub harmonics thereof, tend to effect the linearity of the monitor circuitry and may even swamp the monitor if the intensity is sufficiently great.

The monitoring circuitry relies upon differential amplification of the input signal. A dedicated comparator circuit specifically ensures that an operator alarm is provided if a hang up is experienced at this point. The hang up may result from improper connection and/or operation of the monitoring system, presence of strong EMI, or failure of one or more circuit elements.

To chronically sense potential electromagnetic interference within the pass band of the respiration monitor, supply of the square wave signal to the patient is periodically interrupted to produce a "quiet" period. The monitoring circuitry determines whether any significant signals are present during this quiet period. If not, it is assumed that the environment is free of EMI. If a significant signal is sensed during the quiet period, it is assumed to have been induced by EMI, and the operator is informed by means of an alarm that the monitoring process is compromised by the presence of EMI. As with the other alarm conditions, this alarm may take several forms including a lamp, an aural indication, etc.

The EMI sensing circuitry must be employed during and only during the quiet period. Otherwise, a respiration signal (or just the generated square wave signal without a respiration signal) may be mistakenly assumed to be induced by EMI. Similarly, the respiration sensing circuitry must not be employed during the quiet period or potential lack of detection of valid respiration signals may trigger an apnea alarm.

To ensure that EMI and respiration signal sensing occur at the appropriate times, the quiet periods and associated switches between sensing modes are rendered synchronous to the square wave signal. This is accomplished by counting the output of the regulated oscillator which produces the square wave signal. After a precise number of cycles of the square wave signal, the quiet period is initiated. After a second precise number of additional cycles of the square wave signal, the quiet period is terminated. The counter which initiates and terminates the quiet period for output to the patient is also used to switch between sensing modes.

During periods of respiration signal sensing, the monitor is switched into a mode which senses patient respiration much as is done with earlier devices. However, during the quiet periods, the EMI sensing mode is initiated. Care must be taken to establish a sensing window within the quiet period, which is shorter than the quiet period to ensure that switching transients are eliminated. A level detector determines whether significant EMI is present during the quiet period. For simplicity, EMI detection may be employed using half wave sensing.

As can be appreciated, the sensing time is shared between respiration sensing and EMI sensing, various combinations of time allocation between these modes may be made. In the preferred embodiment, the two modes are simply employed for equivalent time periods. Similarly, the length of the quiet and respiration sensing periods may be easily varied. Again, in the preferred embodiment, a 31.25 KHz square wave signal is employed. A down counter of the basic 31.25 KHz carrier counts to $2^5$ providing approximately 1 KHz switching between modes. It can be seen that these periods may be modified by employing an oscillator operating at a different frequency and/or using a different down count.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
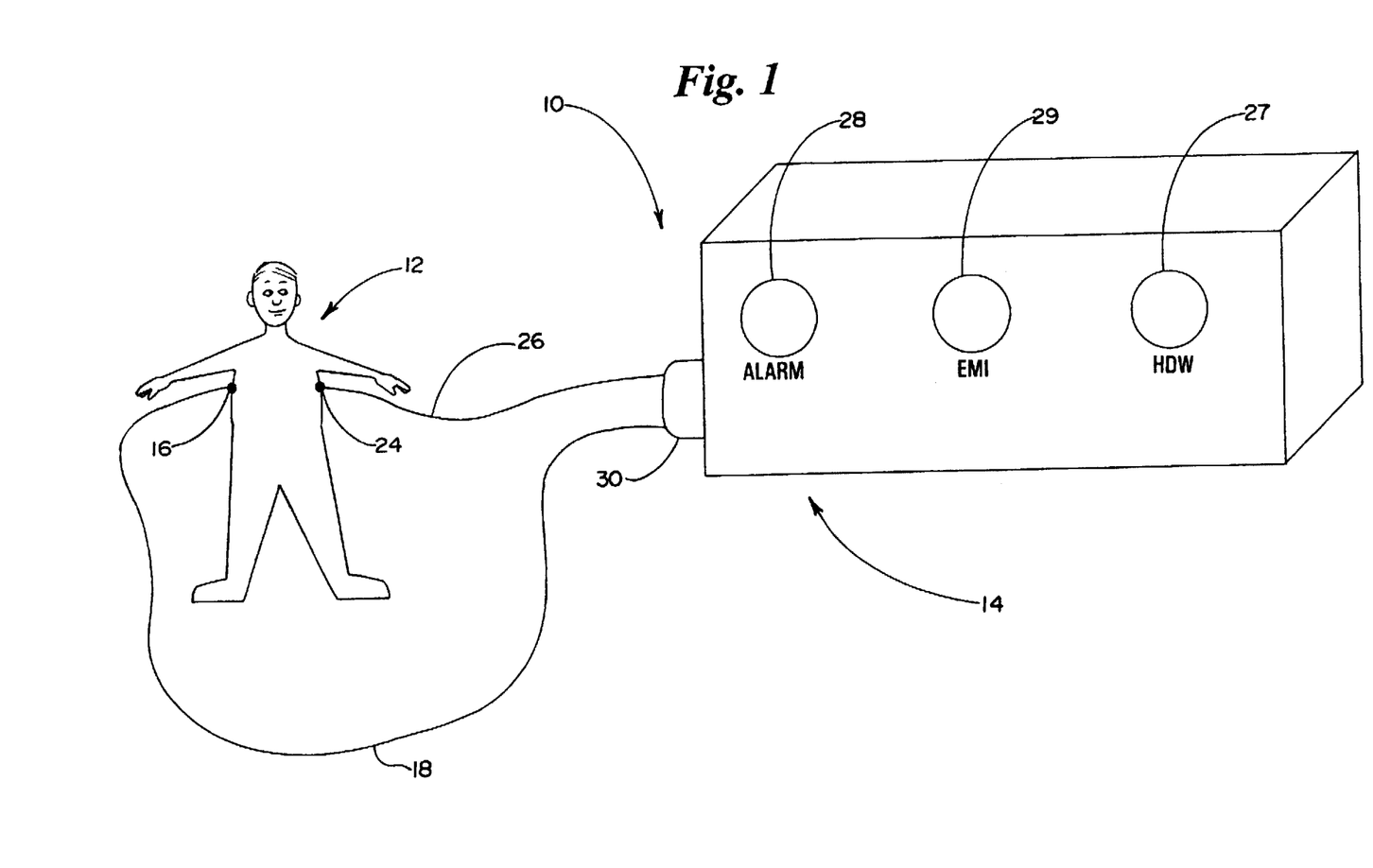
FIG. 1 is a schematic view of a medical monitor according to the present invention.

FIG. 1 is a basic diagram of medical monitoring system 10 according to the present invention. This system is preferably similar to the EdenTec® Model 2000W monitoring system, except as specifically described herein. Patient 12 is normally coupled to medical monitoring system 10 during periods of sleep. Quite often, patient 12 is a child or infant.

Electrode 16 is coupled to the right chest of patient 12. It is electrically coupled to monitor 14 via conductor 18 and connector plug 30. Similarly, electrode 24 is coupled to the left chest and is electrically connected to monitor 14 with conductor 26 and connector plug 30. An optional reference electrode may be provided to monitor 14 through a separate conductor (not shown) and connector plug 30. The reference electrode can be placed over any electrically quiet location such as the right leg. Use of the reference electrode is not required with this circuitry.

To monitor respiration, an alternating current is passed between electrodes 16 and 24 across the thorax of patient 12. As the patient breaths, the effective resistance (i.e. impedance) changes between these electrodes. This change is measured by monitor 14. Any detected cessation of normal respiration of patient 12 is noted by alarm 28 which may be visual, aural, or a combination thereof.

Monitor 14 also monitors whether significant quantities of electromagnetic interference (i.e. EMI) are present. If so, EMI alarm 29 is given to alert attending personnel that respiration monitoring is compromised by the presence of potentially false alarms from EMI. As with alarm 28, alarm 29 may be visual, aural, or a combination thereof. However, it is convenient if alarm 28 and alarm 29 are readily distinguishable by the attending personnel. As is explained in more detail below, EMI alarm 29 may be activated by detection of strong high frequency EMI, substantial EMI within the pass band of the monitor, or a hang up of the differential amplification circuitry.

Hardware alarm 27 is similar to alarms 28 and 29, except that it is activated as a result of detection of an output from the monitoring system during the power up delay time. Operation of this hardware fault detection circuit is explained in more detail below.

Figure 2:
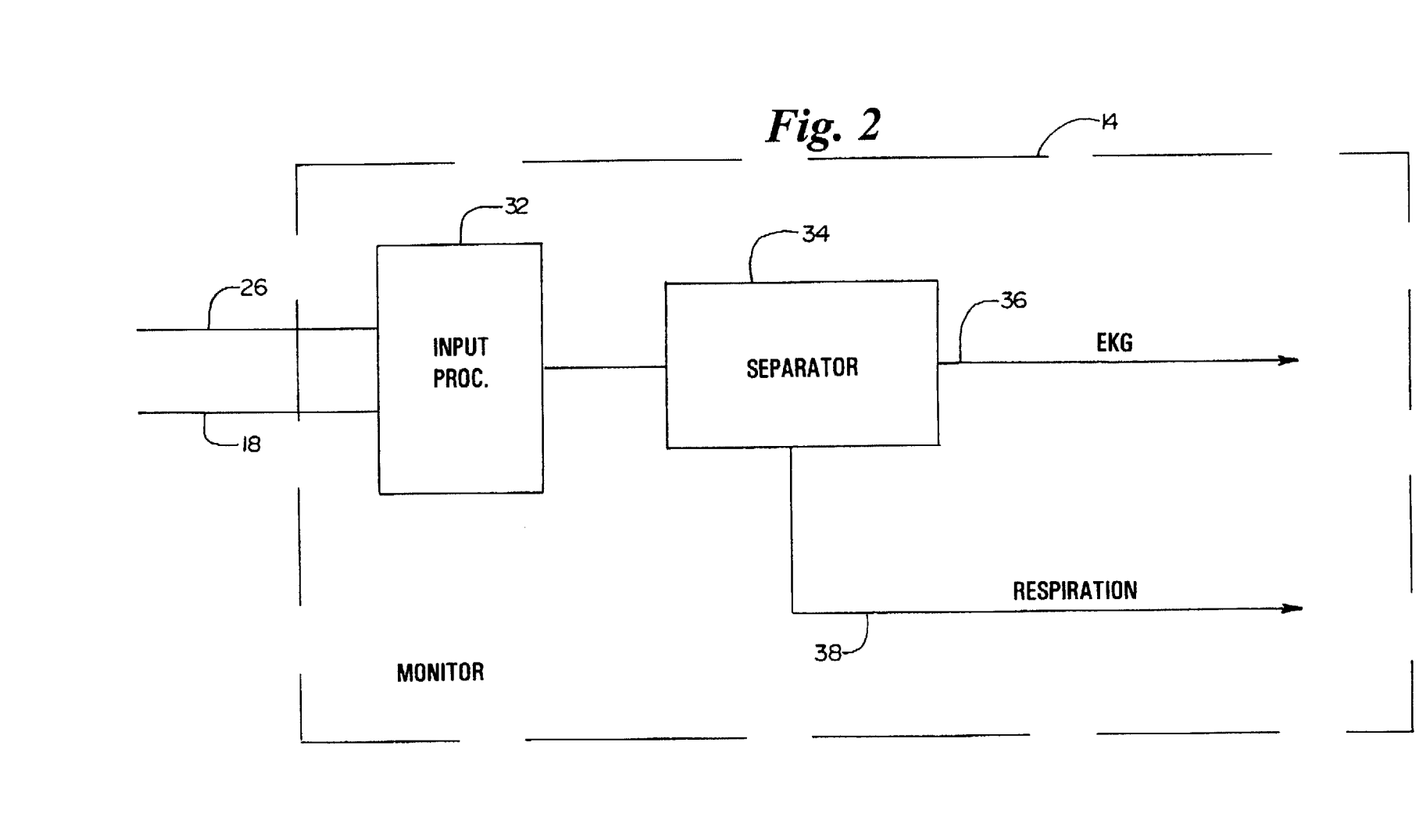
FIG. 2 is a basic block diagram of the medical monitor.

FIG. 2 is a basic block diagram of the operation of monitor Conductors 18 and 26 are coupled to electrodes 16 and 24 respectively (see also FIG. 1). In normal operation these conductors will transfer signals representing respiration activity, cardiac activity (i.e. EKG). Signals induced by EMI may also be present at times. All of these signals are supplied to input processing circuitry 32 for amplification and band pass limiting.

Separator circuitry 34 separates the incoming signals into an EKG component which is sent by cable 36 for further processing and a respiration component which is sent by cable 38 for further processing. Separation is primarily accomplished by dividing the pass band of monitor 14 into a lower frequency component (i.e. EKG) and a higher frequency component (i.e. the drive frequency from which the respiration signal is extracted). The EKG signal is processed in accordance with the teachings of the above referenced Bowman reference. Further details of the respiration signal processing circuitry is provided below.

If significant EMI is present, both the cardiac channel (i.e. cable 36) and the respiration signal processing channel (i.e. cable 38) may contain EMI signals. The potential EMI induced signals present on the respiration signal processing channel are processed as described in more detail below.

Figure 3:
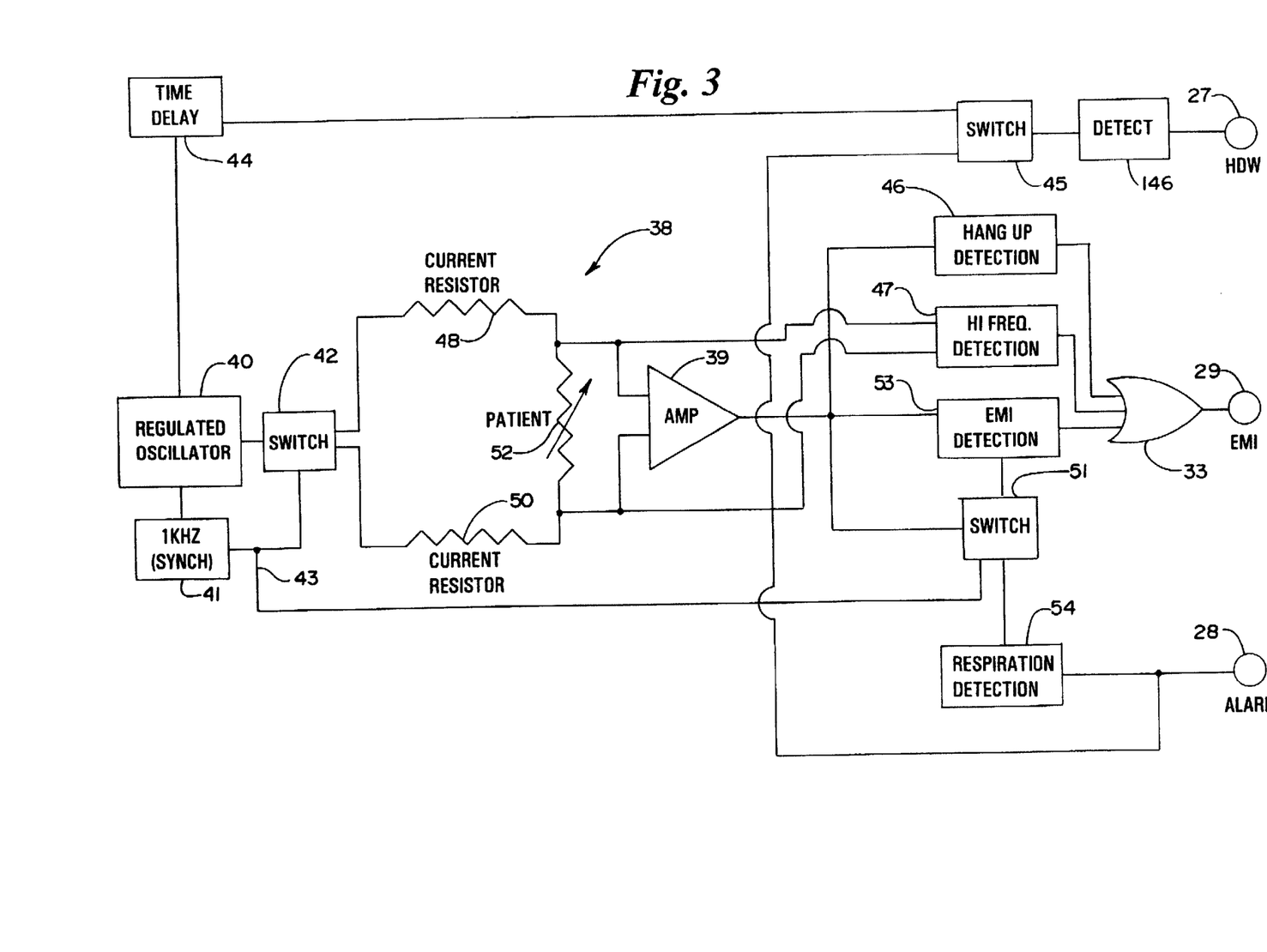
FIG. 3 is a basic schematic of the respiration monitor circuit.

FIG. 3 is a simplified schematic diagram showing the operation of the respiration signal processing. Regulated oscillator 40 provides a regulated square wave alternating current output. Preferably this output has a frequency of 31.25 KHz. This continuous output is switched by output switch 42 to provide periods of carrier output for respiration monitoring and quiet periods for EMI monitoring.

Output switch 42 is controlled by the output of synchronized 1 KHz source 41. In the preferred embodiment and not to be inferred as limiting of the present invention, 1 KHz source 41 counts $2^5$ cycles of the 31.25 KHz carrier before opening the coupling between regulated oscillator 40 and the patient. After another $2^5$ cycles of the carrier are counted, switch 42 again closes thus terminating the quiet period.

The 31.25 KHz signal, when switched on by output switch 42, proceeds through current resistor 48, patient 12 (represented by variable resistor 52), and current resistor 50 to complete the circuit. The signal across patient 12 (i.e. variable resistor 52) is amplified by amplifier 42. Isolation devices (not shown) separate patient 12 from the remainder of the circuitry and from earth ground for patient safety. In practice, this function is preferably accomplished by isolation transformers and/or electro optic isolators.

In the actual system, variable resistor 52 consists of conductors 18 and 26, electrodes 16 and 24, and the impedance across the body of patient 12 (see also FIG. 1). It is intended that the variation in resistance of variable resistor 52 be produced primarily by the respiration activity of patient 12, although cardiac signals and EMI induced signals will also be present as explained above.

Input switch 51 is also driven by the output of the 1 KHz switched 31.25 KHz synchronized source 41 via line 43. In this way input switch 51 switches synchronously with output switch 42 between respiration detection circuit 54 and EMI detection circuit 53. During periods when output switch 42 is closed (i.e. the carrier is supplied to the patient), the monitor is in the respiration sensing mode, and switch 51 supplies the input signal to respiration detection circuit 54. Whenever output switch 42 is open, a quiet period is in process and switch 51 directs the input signal to EMI detection circuitry 53 to determine whether EMI induced signals are present. As explained in more detail below, the sense window is actually shorter than the quiet period to reject switching transients.

During respiration mode sensing, respiration detection circuit 54 measures the change in voltage drop across variable resistor 52 within the pass band of the respiration monitoring circuitry. This change in voltage drop is proportional to the change in resistance of variable resistor 52, because current resistors 48 and 50, being the principal other circuit elements constituting the load, are of constant resistance. During quiet periods, EMI detection circuitry 53 activates EMI alarm 29 via or gate 33, if it determines that a substantial level of signal is present.

EMI alarm 29 may also be actived via or gate 33 as a result of the detection of a hang up condition by hang up detection circuit 46. Such a hang up condition can result from the presence of EMI or a hardware failure which causes one side of the differential amplification circuitry to remain stuck at its saturated state.

The third condition causing activation of EMI alarm 29 by or gate 33 results from detection by high frequency detection circuit 47 of the presence of a large amplitude signal at the input of the monitor which is above the pass band of interest for respiration monitoring. An alarm is given for this condition to notify the operator that such high frequency EMI may effect the accuracy of the monitoring activity.

The fourth validity testing feature is produced by a delay of about ten (10) seconds generated by time delay circuit 44. This circuit prevents the output of regulated oscillator 40 from being placed on the patient cable during the power up activity. This delay signal is also presented to switch 45 which has available the output of amplifier 39. If detector 48 determines that a substantial signal is present during the ten second delay, a hardware failure condition is assumed and alarm 27 is activated. Though this condition may also be generated by EMI during the power up sequence, it is assumed that in most instances, the alarm will be the result of a hardware failure.

Figure 4:
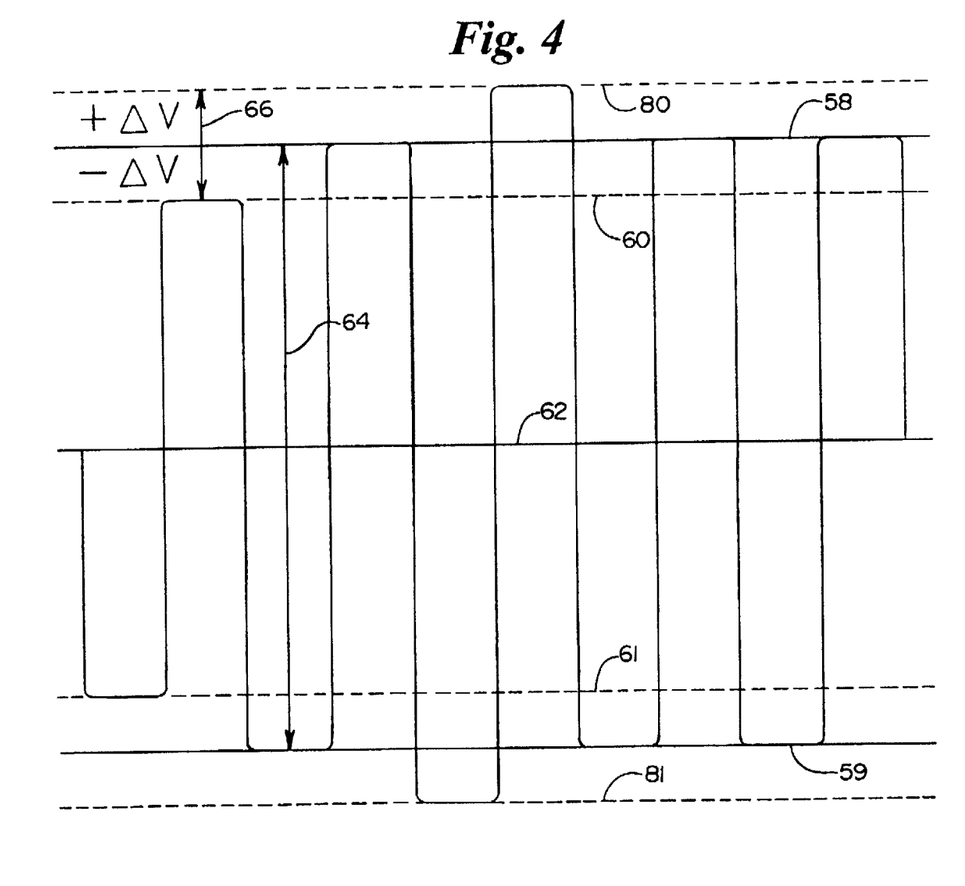
FIG. 4 is a view of the monitoring carrier.

FIG. 4 is a graphical representation of several cycles of the 31.25 KHz carrier signal as presented to respiration detection circuit 54 in the respiration sensing mode (see also FIG. 3). This yields a period of about 32 microseconds. The square wave of the 31.25 KHz carrier signal has a nominal voltage 64 which varies between positive fixed voltage level 58 and negative fixed voltage level 59 on either side of null voltage level 62. Impressed upon the carrier signal is a variable voltage 66, which amplitude modulates the 31.25 KHz carrier signal on both sides of null level 62. It is assumed that variable voltage 66 will vary between positive levels 60 and 80 and between negative levels 61 and 81 under normal conditions as a result of respiration (i.e. without presence of transient artifacts).

Nominal voltage 64 is a relatively stable component associated with the nominal resistance across patient 12, along with the resistance of the electrodes, conductors, etc. Variable voltage 66 is proportional to the change in resistance across the body of patient 12 over time. A primary component of this resistance change results from respiration activity. However, it also contains components associated with transient artifacts.

Figure 5:
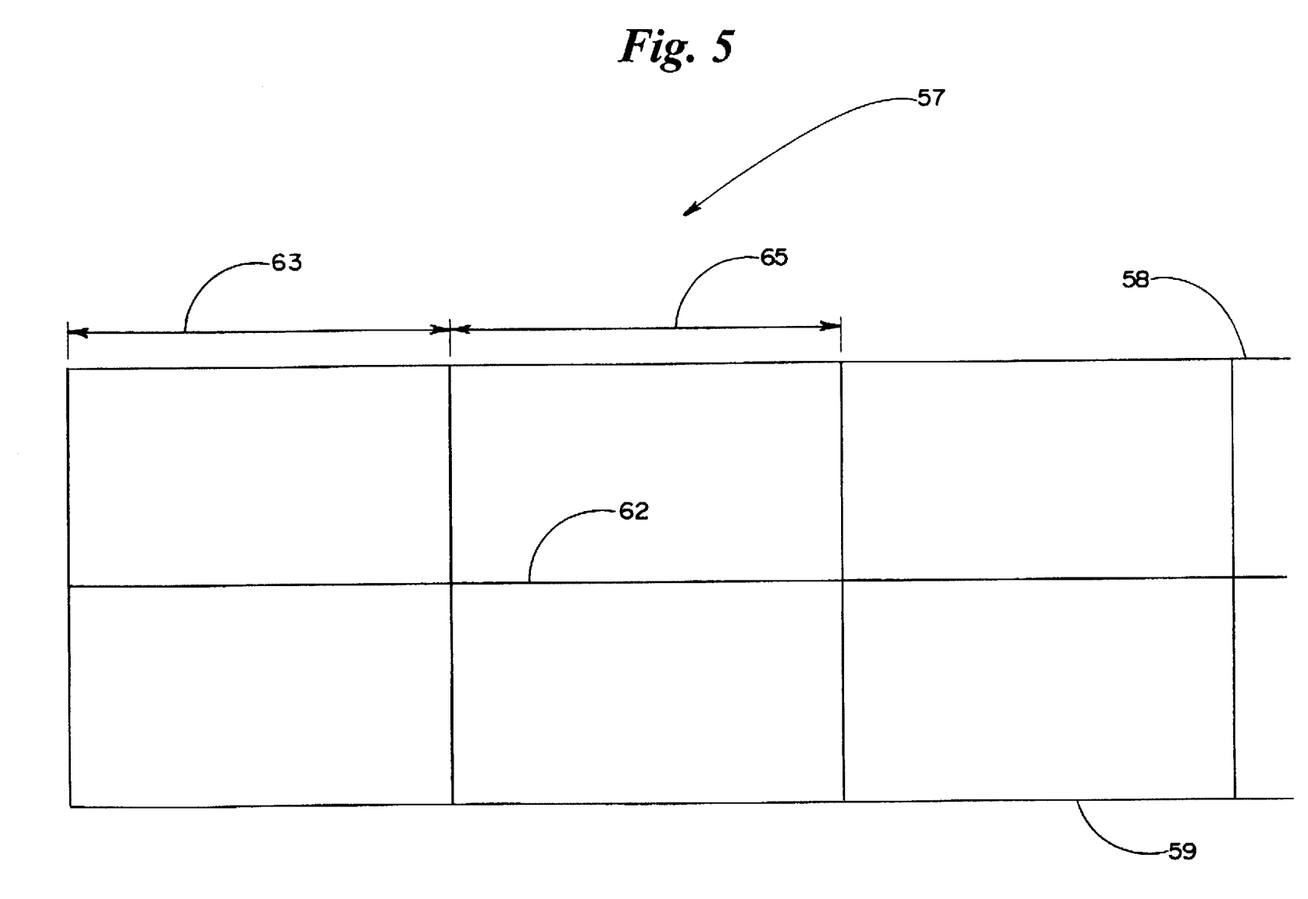
FIG. 5 is a view of the monitoring carrier modulated showing a quiet period.

FIG. 5 is a graphical representation 57 of many cycles of the 31.25 KHz carrier signal as switched on and off by output switch 42 (see also FIG. 3). Nominal voltage 64 is between voltage levels 58 and 59. For clarity, no respiration signal is present in graphical representation 57.

Respiration sensing period 63 and quiet period 65 are of equivalent duration in the preferred mode. Each has a duration of approximately 500 microseconds. By using a 31.25 KHz carrier frequency and counting $2^5$ cycles of the carrier with synchronous 1 KHz source (see also FIG. 3), the duration of period 63 plus period 65 is 1.024 milliseconds. Therefore, period 63 and period 65 are each 512 microseconds.

Those of skill in the art will readily appreciate that period 63 and period 65 need not be equal. Furthermore, other time durations can be achieved using different carrier frequencies and different count down factors. However, the circuitry is greatly simplified by synchronously timing the quiet period to minimize variations in the switching transients.

Figure 6:
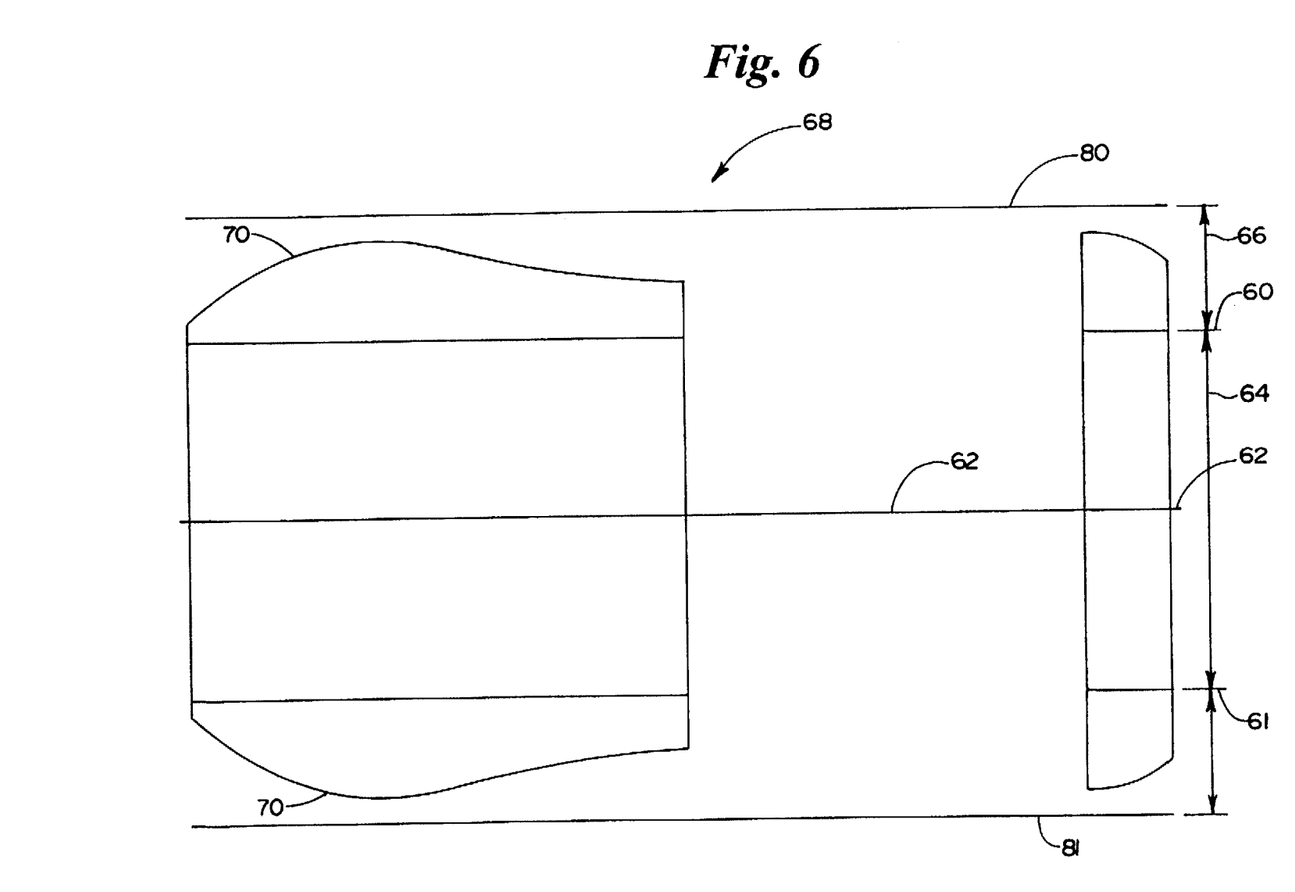
FIG. 6 shows the signal of FIG. 5 as modulated by a respiration signal.

FIG. 6 is a graphical representation 68 of the carrier of FIG. 5 with a respiration signal 70 impressed thereupon. Upon seeing the respiration signal 70 impressed upon the carrier, those of skill in the art will appreciate that some care must be exercised in choosing the duration of the respiration sensing period to ensure that the respiration signal can be adequately sensed.

Figure 7:
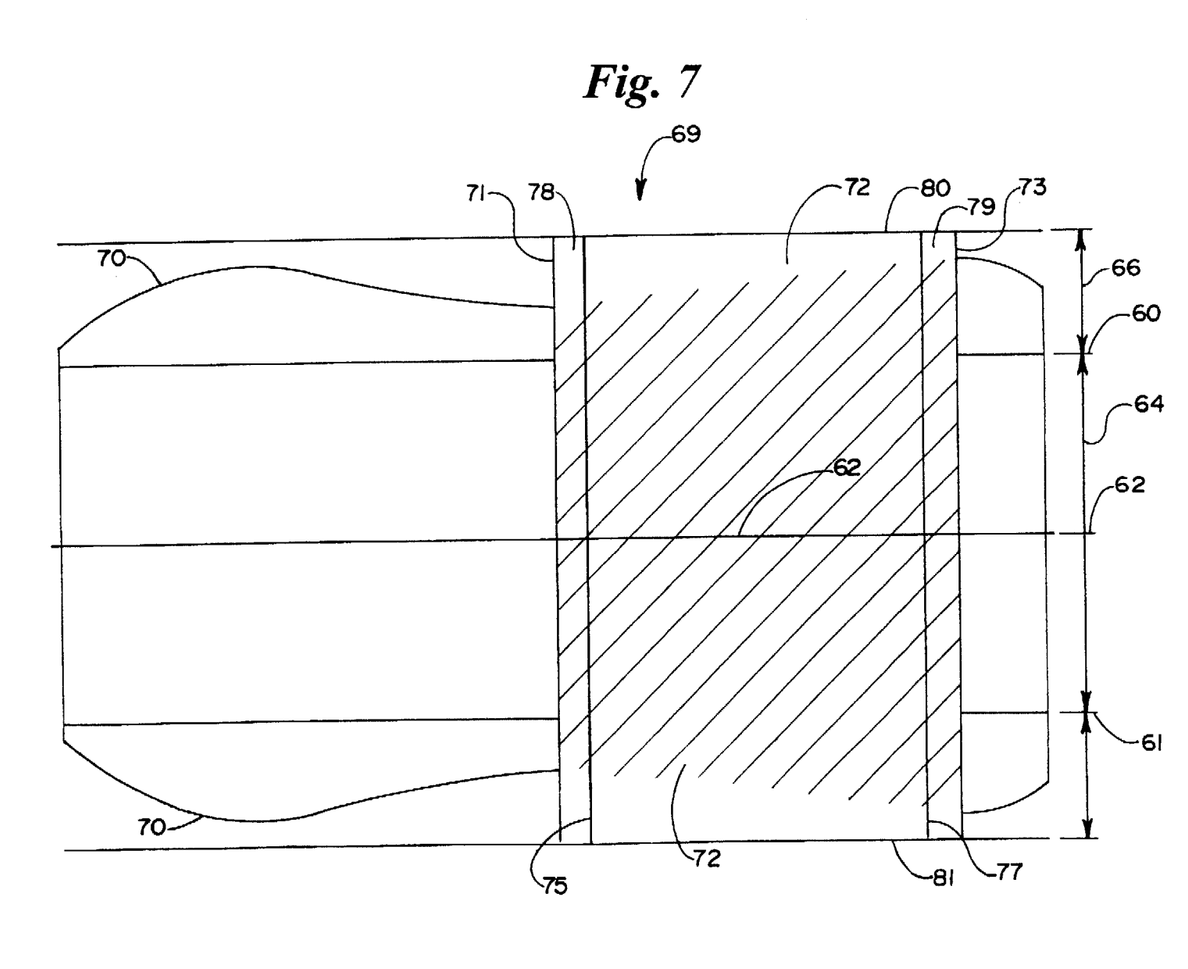
FIG. 7 shows the signal of FIG. 6 with EMI present.

FIG. 7 is a graphical representation 69 of the signal of FIG. 6 showing the presence of detectable EMI signals. The EMI detector senses substantial signal content within EMI sensing window 72 thus indicating potentially harmful EMI induced monitoring errors. EMI sensing window 72 is defined as that time window between time 75 and time 77. This is less than the entire quiet period which exists between time 71 and time 73. Separate definitions for the quiet period and EMI sensing window 72 produces leading guard period 78 and trailing guard period 79. These guard periods are established to ensure that switching transients are not detected as either a respiration signal or EMI. All other referenced elements are as previously described.

Figure 8:
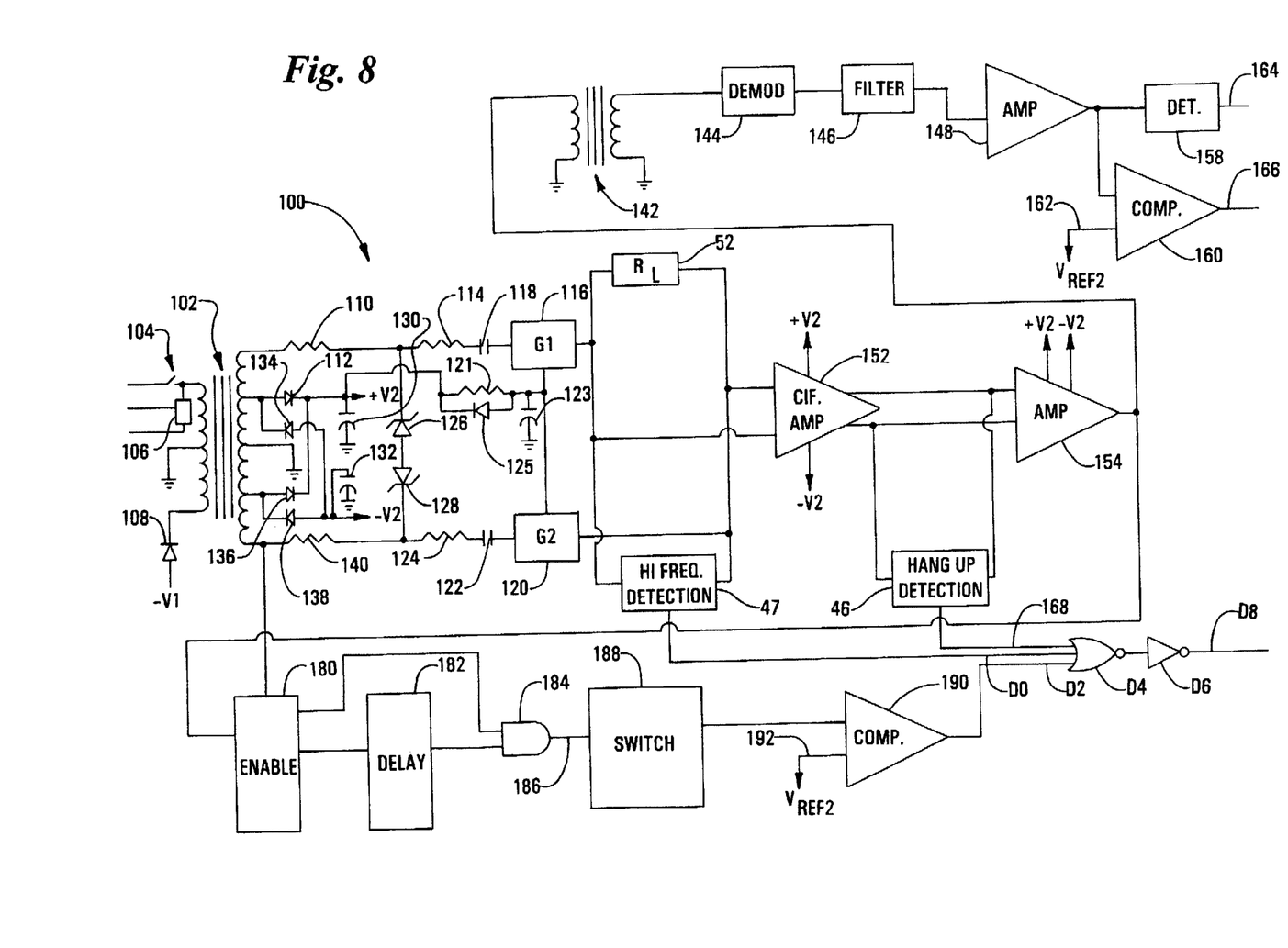
FIG. 8 is a detailed schematic diagram of the EMI detection circuitry.

FIG. 8 is a schematic diagram 100 showing the respiration monitoring circuitry, along with the protection devices, according to the preferred embodiment of the present invention. The 31.25 KHz square wave signal is supplied to switching circuit 106 (described in more detail below), which switches between the respiration monitoring period and quiet period. Transformer 102 isolates the patient from the signal generation circuit. Switch 104 is the on/off switch coupled to the positive power supply. Diode 108 couples to the negative power supply.

The secondary of transformer 102 drives the load consisting primarily of variable resistor 52 series current resistors 110, 114, 140 and 124. Capacitors 118 and 122 couple the carrier signal to internal gain controls 116 and 120. Zener diodes 126 and 128 provide the voltage reference for the patient current source and clamp the patient cable to a maximum safe internal voltage drop to prevent circuit damage if the system is improperly used. A second winding of the secondary of transformer 102 is used to accommodate a bias supplied by a second positive and negative power supply via diodes 112, 134, 136, and 138. Capacitors 130 and 132 decouple high frequency transients. Time delay circuit 44 (see also FIG. 3) consists of protection diode 125 and resistor 121 and capacitor 123, which are chosen to provide approximately ten (10) seconds of delay upon power up of the system. Signals greater than a predetermined threshold amplitude detected during this ten second delay are assumed to result from a hardware failure.

High frequency detection circuit 47 (described in more detail below) is coupled across variable resistor 52. If the presence of high frequency signals of substantial amplitude is detected, NOR gate 174 is notified via line 170 that an EMI alarm should be generated. The alarm signal is inverted by inverter 176 and transferred via line 178.

The signal across variable resistor 52 is also differentially amplified by differential amplifier 152. The output is converted to a single ended signal by amplifier 154 which is presented to the respiration and EMI detection circuits. If differential amplifier 152 should hang up, this condition is detected by hang up detection circuit 46 (discussed in more detail below) and NOR gate 174 is notified via line 168 that an EMI alarm should be generated.

Respiration processing begins with transformer 142 which provides isolation from both high frequencies and direct current bias. The signal is demodulated by demodulation circuit 144, filtered by filter circuit 146, and amplified by amplifier 148. Detection of the respiration signal is accomplished by detection circuit 158, and the results are transferred via line 164. During the ten second delay at power up described above, the signal is presented to comparator circuit 160. The signal is compared in amplitude with the second reference voltage on line 162. If the signal amplitude exceeds the reference voltage, comparator circuit 160 transfers a hardware error signal via line 166. This hardware error signal is used to activate the hardware alarm (see also FIG. 1) during the ten second power up delay period. At all other times the state of line 166 is considered invalid.

An output of amplifier 154 is also provided to switch 188 for detection of EMI energy during the quiet period. Switch 188 determines the EMI sensing window, which is a portion of the quiet period as explained above. To produce the timing for the EMI sensing window, the 31.25 KHz carrier, as switched at the 1 KHz rate, is transferred to retriggerable multivibrator 180 from the secondary of transformer 102. The delayed output is used to enable and gate 184 and also to signal non-retriggerable multivibrator 182 to generate a second signal which has an even greater delay. The output of non-retriggerable multivibrator 182 is also provided to and gate 184.

The output of and gate 184, placed on line 186, is a pulse having a width which is less than that of the quiet period. The leading edge of the pulse can be no earlier than the leading edge of the output of non-retriggerable multivibrator 182 (i.e. time 75 of FIG. 7). The trailing edge can be no later than the trailing edge of the output of retriggerable multivibrator 180 (i.e. time 77 of FIG. 7).

The output of amplifier 154 is thus switched by switch 188 in accordance with the output of and gate 184 to the input of comparator circuit 190. Comparator circuit 190 compares the output of amplifier 190 to the second reference voltage during the EMI sensing window. If the level exceeds the second reference voltage, an EMI condition is assumed. The output of comparator circuit 190 is transferred to NOR gate 174 via line 172. This permits the EMI alarm to be activated.

Figure 9:
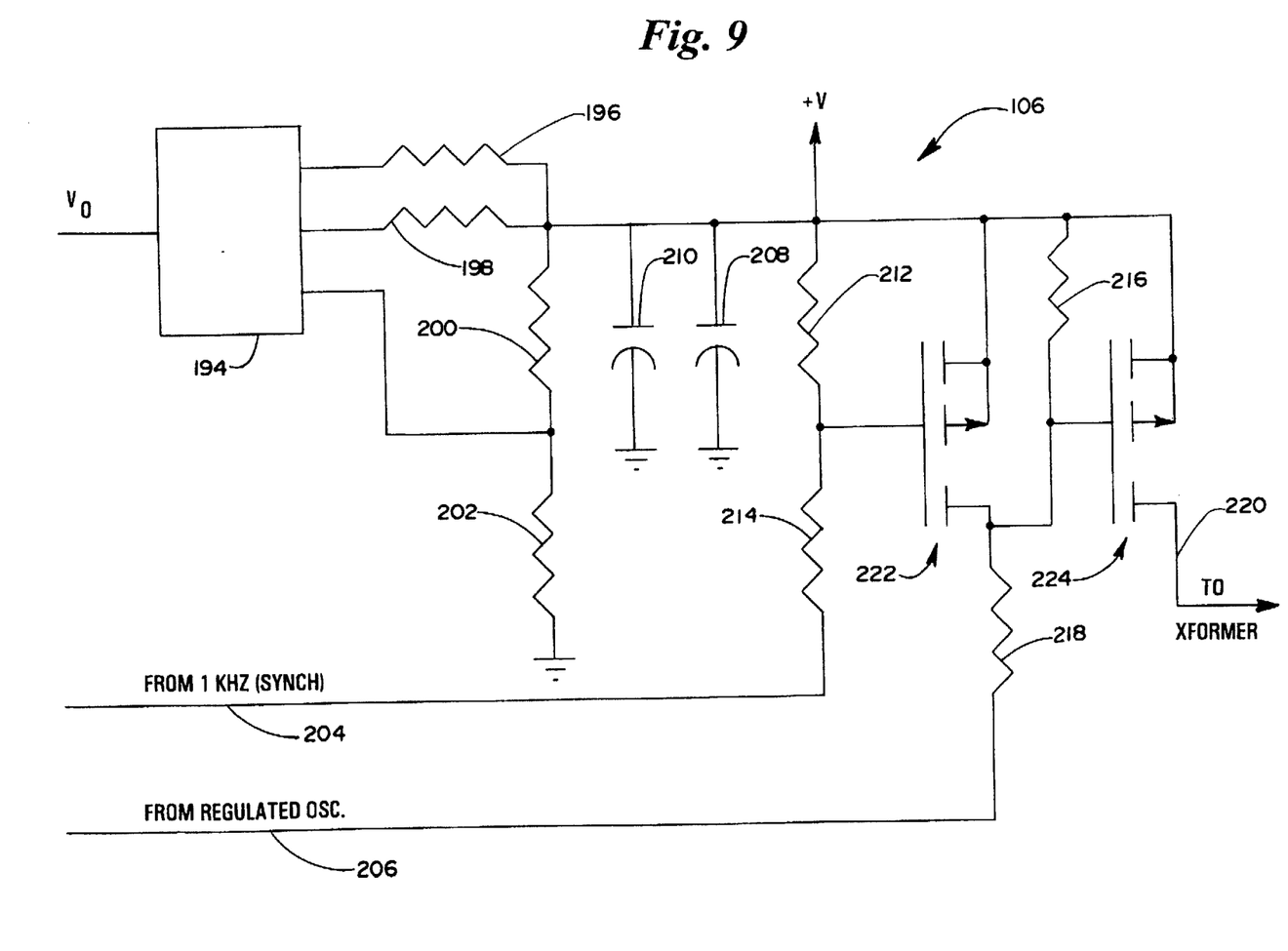
FIG. 9 shows the circuitry associated with switching the carrier to provide monitoring and quiet periods.

FIG. 9 is a schematic diagram 106 of the circuitry associated with the output of the 31.25 KHz carrier. The square wave pattern is generated by regulated oscillator 40 and supplied by line 206 (see also FIG. 3). This signal is applied through current resistor 218 to the drain of field effect switch 222 and to the gate of field effect switch 224. Synchronous 1 KHz source 41 counts the number of cycles of the 31.25 KHz square wave pattern. Bit position $2^5$ of down counter 41 drives the gate of field effect switch 222, through line 204 and series resistor 214. The gate of field effect switch 222 is pulled up to the positive voltage (i.e. +v) of line 102 through current resistor 212 whenever that output is high, turning off field effect switch 222.

Whenever field effect switch 222 is off, the gate of field effect switch 224 varies at a 31.25 KHz rate as driven by regulated oscillator 40 thus alternately applying +v to transformer 102 (see also FIG. 8) from the source to the drain of field effect switch 224. This corresponds to the respiration sensing mode as is discussed in more detail below.

Conversely, when bit $2^5$ of synchronous 1 KHz source 41 is low, field effect switch 222 is closed drawing the gate of field effect switch 224 to +v via resistor 116. This causes field effect switch 224 to open regardless of the output of regulated oscillator 40. A quiet period is produced whenever field effect switch 224 is held open in this manner.

Figure 10:
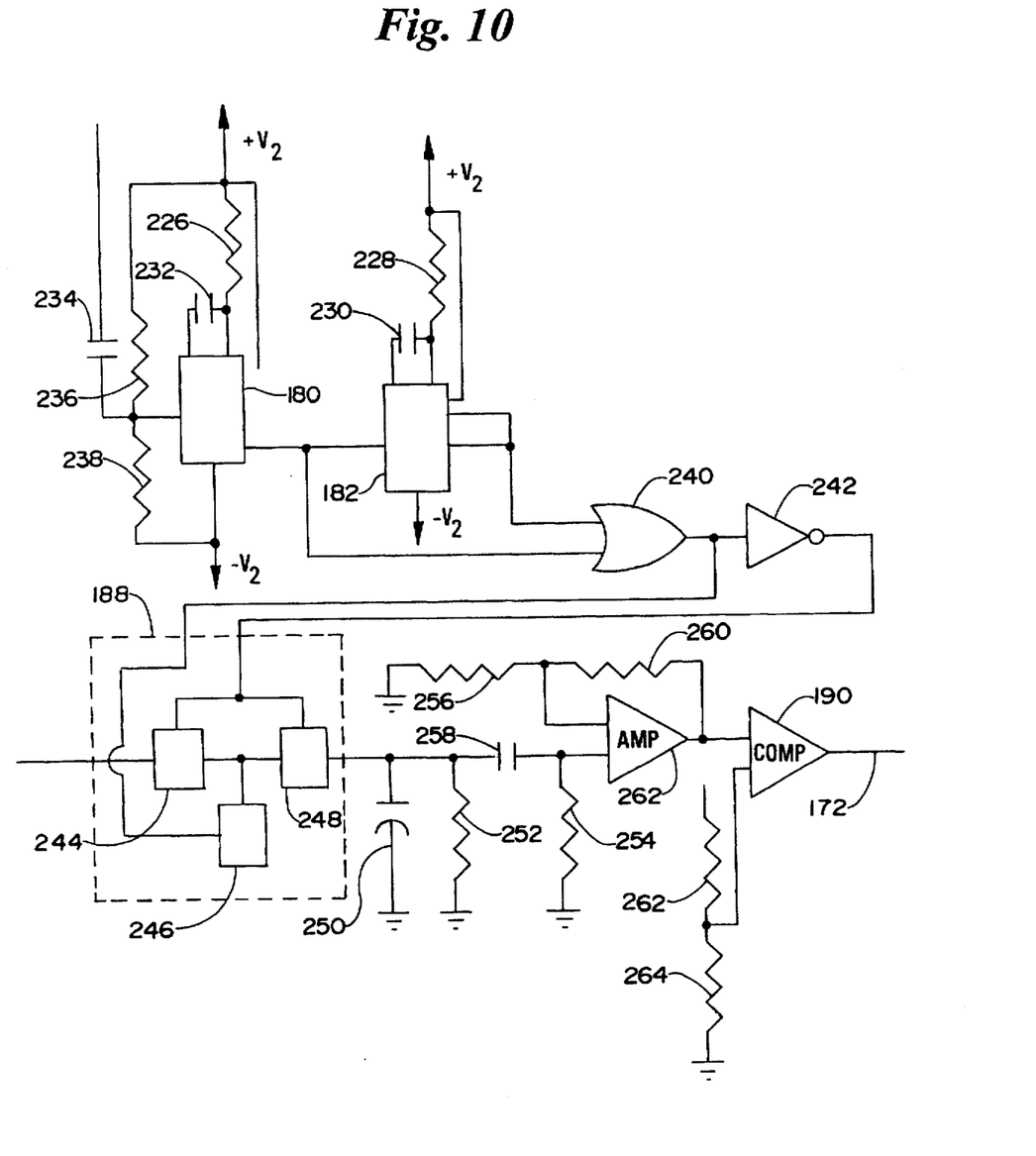
FIG. 10 is a detailed schematic diagram of the EMI sense window circuit.

FIG. 10 is a schematic diagram showing additional detail of the circuitry which creates the EMI sensing window, switches the sensing input, and makes the EMI threshold comparison. Retriggerable multivibrator 180 is strapped using resistors 226, 236, and 238, along with capacitor 232 to produce the desired delay. Coupling to the signal source is via capacitor 234 (see also FIG. 8). Similarly, non-retriggerable multivibrator 182 has its characteristics determined by resistor 238 and capacitor 230. AND gate 184 (see also FIG. 8) is actually implemented using OR gate 240 and inverter 242, which provides the equivalent logical function.

Switch 188 is implemented using individual switching elements 244, 246, and 248, as shown. The input signal is received by switching element 244. The output of switching element 248 is the sensing signal during the EMI sensing window. Filtering is provided by capacitors 250 and 258, along with resistors 252 and 254. Amplifier 262, along with reference resistors 256 and 260 prepare the signal for threshold determination.

The presence of significant EMI is assumed if the level presented to comparator circuit 190 by amplifier 262 during the EMI sensing window exceeds the reference voltage established across resistors 262 and 264. If this threshold is reached, comparator 190 sets line 172 to indicate that the EMI alarm should be activated (see also FIGS. 1, 3, and 8).

Figure 11:
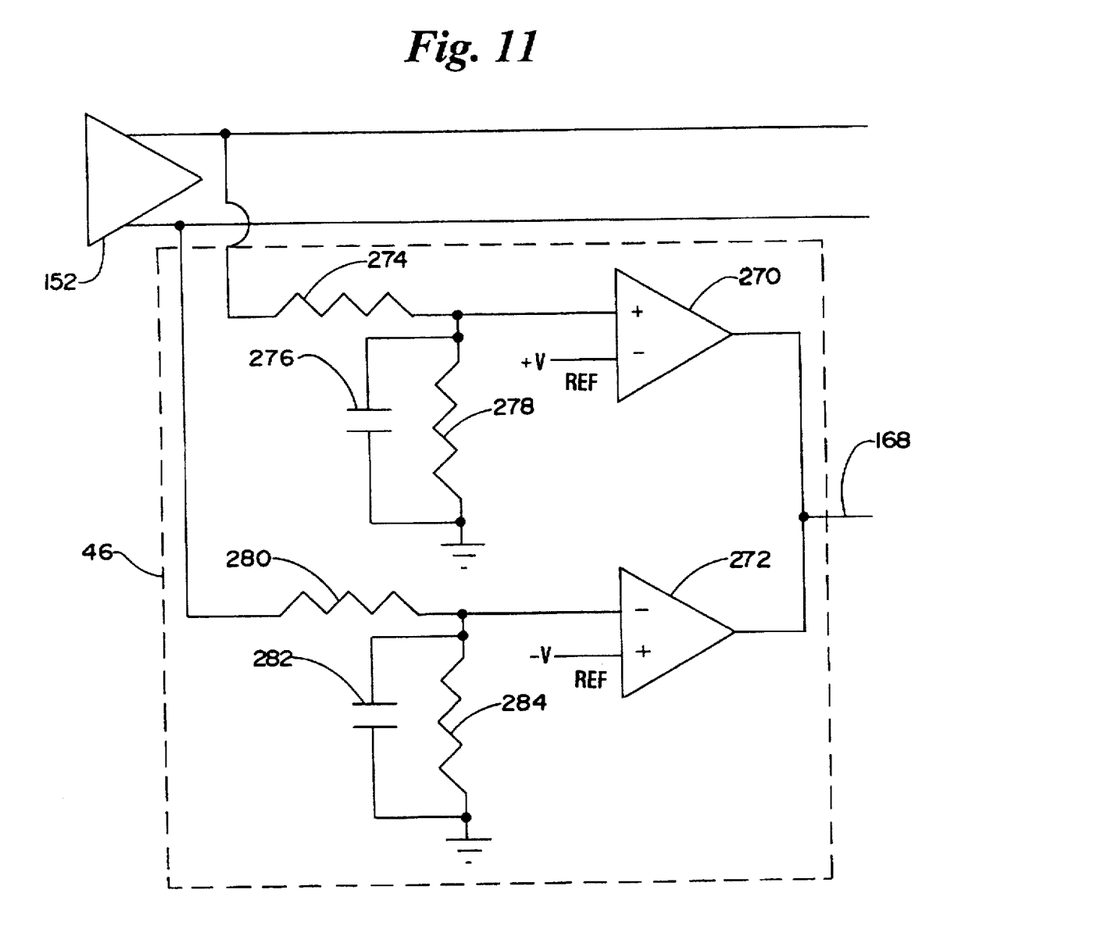
FIG. 11 is a schematic diagram of the hang up detection circuit.

FIG. 11 is a detailed schematic diagram of hang up detection circuit 46. It functions by comparing each side of differential amplifier 152 to a reference voltage of opposite polarity. A hang up condition is defined as either side of differential amplifier 152 stuck at or in excess of its respective reference voltage. In most cases, this will result from EMI, although certain hardware failures can induce the same condition.

Series resistor 274 couples the positive going output of differential amplifier 152 to positive comparator 270. The input signal is filtered by capacitor 276 and resistor 278. Comparison is made with the positive reference voltage. Similarly, the negative going output of differential amplifier 152 is coupled via resistor 280 to negative comparator 272. Filtering is provided by capacitor 282 and resistor 284.

Figure 12:
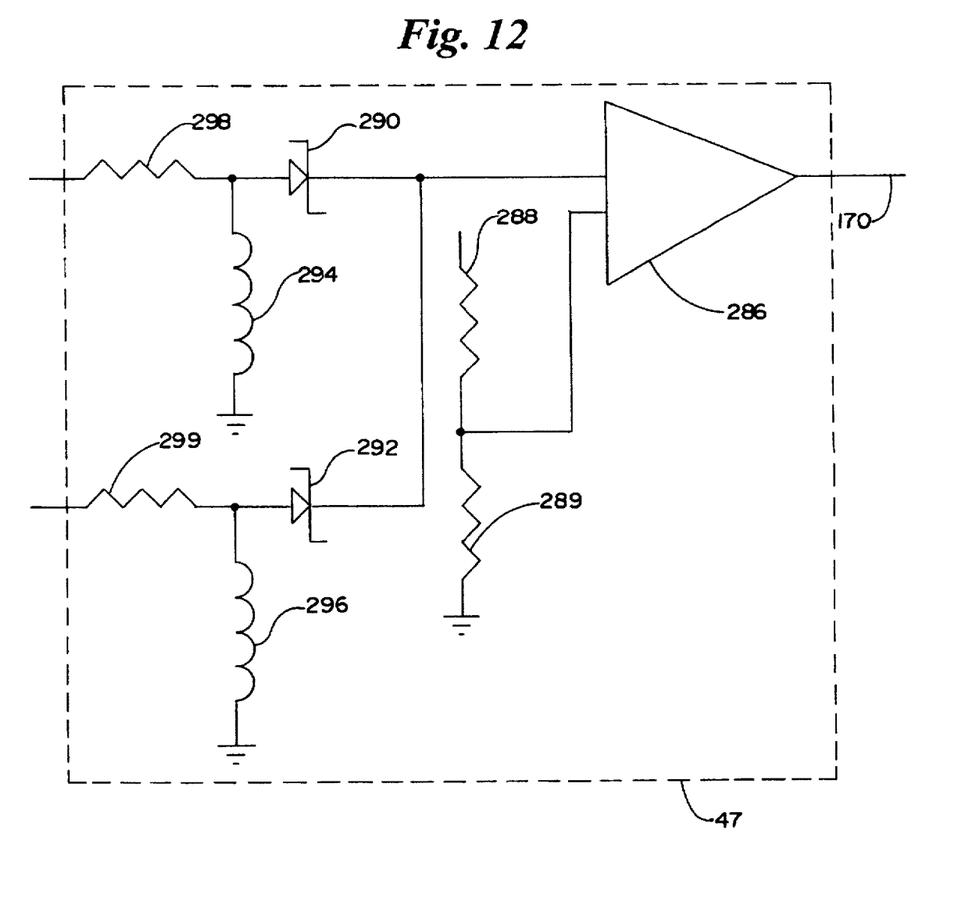
FIG. 12 is a schematic diagram of the high frequency EMI detection circuit.

FIG. 12 is a schematic diagram of the high frequency EMI detection circuit 47. This circuit checks the input signal for the presence of a substantial level of EMI well above the pass band of the respiration monitor. This test is deemed significant, because large amplitude high frequency components can produce troublesome subharmonics and tend to overload the respiration detection circuitry.

The input to high frequency detection circuit 47 is via resistors 298 and 299 which couple directly to the patient cable (see also FIGS. 3 and 8). All low frequency components are bypassed by inductors 294 and 296, thus presenting only the high frequency components to high frequency switching diodes 290 and 292. This input to comparator circuit 286 is compared to a reference voltage established across resistors 288 and 289. If the high frequency signal input exceeds the reference threshold, comparator circuit 286 indicates via line 170 that the EMI alarm should be activated.

Having thus described the preferred embodiments of the present invention, those of skill in the art will be readily able to apply the teachings found herein to yet other embodiments within the scope of the claims hereto to attached and wherein:

We claim:
1. An apparatus comprises:
   a. monitoring means for monitoring respiration of a patient, said monitoring means comprising:
      i. generating means for generating a carrier signal;
      ii. applying means coupled to said generating means for applying said carrier signal across the thorax of said patient;
      iii. measuring means coupled to said applying means for measuring changes in said carrier signal as applied across said thorax of said patient;
   b. sensing means responsively coupled to said monitoring means for sensing the presence of non-physiologically induced electromagnetic interference which may render said monitoring means inaccurate, said sensing means comprising:
      i. interrupting means for interrupting said applying means during a quiet period; and
      ii. determining means for determining the presence of a substantial non-physiologically induced electromagnetic interference during said quiet period.

2. An apparatus according to claim 1 wherein said interrupting means is coupled to said monitoring means to interrupt said monitoring means during said quiet period.

3. An apparatus according to claim 2 further comprising an alarm for notifying an operator whenever said determining means determines said presence of said substantial non-physiologically induced electromagnetic interference during said quiet period.

4. An apparatus according to claim 2 wherein said interrupting means comprises a down counter coupled to said generating means for counting cycles of said carrier signal.

5. An apparatus according to claim 4 wherein said determining means further comprises a level detector.

6. An apparatus according to claims 1, 2, 3, 4 or 5 wherein said monitoring means further comprises means for determining the presence of a predetermined minimum amplitude of high frequency non-physiologically induced electromagnetic interference.

7. An apparatus according to claim 6 wherein said monitoring means further comprises means for determining the presence of a component failure.

* * * * *